US012514996B2

(12) United States Patent
Berry et al.

(10) Patent No.: US 12,514,996 B2
(45) Date of Patent: *Jan. 6, 2026

(54) METERED DOSE INHALERS OF FLUTICASONE OR AN ESTER THEREOF

(71) Applicant: GLENMARK PHARMACEUTICALS LIMITED, Maharashtra (IN)

(72) Inventors: Julianne Berry, Westfield, NJ (US); Rajesh Ankam, Maharashtra (IN); Sushrut Kulkarni, Maharashtra (IN); Michael Crick, Glen Rock, NJ (US); Hemant Pawar, Maharashtra (IN); Rajesh Raikar, Maharashtra (IN)

(73) Assignee: GLENMARK PHARMACEUTICALS LIMITED, Mumbai (IN)

(*) Notice: Subject to any disclaimer, the term of this patent is extended or adjusted under 35 U.S.C. 154(b) by 0 days.

This patent is subject to a terminal disclaimer.

(21) Appl. No.: 18/929,508

(22) Filed: Oct. 28, 2024

(65) Prior Publication Data

US 2025/0050040 A1 Feb. 13, 2025

Related U.S. Application Data

(63) Continuation of application No. 17/651,044, filed on Feb. 14, 2022.

(30) Foreign Application Priority Data

Feb. 15, 2021 (IN) ............................ 202121006372

(51) Int. Cl.
*A61M 15/00* (2006.01)
*A61K 9/00* (2006.01)
*A61K 31/56* (2006.01)

(52) U.S. Cl.
CPC ........... *A61M 15/009* (2013.01); *A61K 9/008* (2013.01); *A61K 31/56* (2013.01); *A61M 15/0068* (2014.02); *A61M 2205/0238* (2013.01)

(58) Field of Classification Search
None
See application file for complete search history.

(56) References Cited

U.S. PATENT DOCUMENTS 6,131,566 A * 10/2000 Ashurst .................. A61P 11/00 128/200.14
2003/0089368 A1* 5/2003 Zhao .................. A61M 15/009 604/59

(Continued)

FOREIGN PATENT DOCUMENTS

WO 0119342 A2 3/2001
WO 03002169 A2 1/2003
WO WO-2009003657 A1 * 1/2009 .......... A61M 15/009

OTHER PUBLICATIONS

Copelli, Actuator Performance Comparison by an Integrated Multivariate Approach , 2016.*
"Solution based . . . morphology", Marasini, 2022.*

*Primary Examiner* — Bradley H Philips
(74) *Attorney, Agent, or Firm* — Blank Rome LLP

(57) ABSTRACT

The invention relates to metered dose inhaler comprising a stable pharmaceutical composition of fluticasone or its pharmaceutically acceptable ester contained in a canister fitted with a metering valve, an actuator and dose counter. The invention also relates to a process for preparing said pharmaceutical composition and its use in the treatment of respiratory disorders such as asthma in a subject (e.g., a human).

10 Claims, 2 Drawing Sheets

(56) References Cited

U.S. PATENT DOCUMENTS

| | | | | |
|---|---|---|---|---|
| 2003/0180228 | A1* | 9/2003 | Cripps | B65D 77/003<br>128/200.23 |
| 2006/0118107 | A1* | 6/2006 | King | A61M 15/0005<br>128/200.14 |
| 2009/0020114 | A1* | 1/2009 | Brambilla | A61P 11/00<br>128/200.23 |
| 2011/0020244 | A1* | 1/2011 | Flanders | A61P 11/06<br>424/45 |
| 2014/0060531 | A1* | 3/2014 | Brambilla | A61M 15/0065<br>128/203.12 |
| 2014/0299128 | A1* | 10/2014 | Jinks | C09K 3/30<br>141/3 |
| 2017/0021117 | A1* | 1/2017 | Howgill | G06M 1/166 |
| 2017/0209409 | A1* | 7/2017 | Hartman | A61K 47/44 |
| 2019/0030047 | A1* | 1/2019 | Khairatkar-Joshi | A61K 31/58 |
| 2020/0147325 | A1* | 5/2020 | Wilson | A24F 40/40 |
| 2022/0331237 | A1* | 10/2022 | Luciuk | A61M 15/009 |
| 2023/0081910 | A1* | 3/2023 | Cocks | A61K 31/137<br>128/200.23 |
| 2023/0271770 | A1* | 8/2023 | Zhang | A61M 15/009<br>128/200.23 |

* cited by examiner

METERED DOSE INHALERS OF FLUTICASONE OR AN ESTER THEREOF

This patent application is a continuation of U.S. patent application Ser. No. 17/651,044, filed Feb. 14, 2022, which claims priority to Indian Provisional Patent Application No. 202121006372, filed on Feb. 15, 2021, each of which is incorporated by reference herein.

FIELD OF THE INVENTION

The present invention relates to a metered dose inhaler comprising a stable pharmaceutical composition of fluticasone or a pharmaceutically acceptable ester thereof, contained in a canister fitted with a metering valve, an actuator and a dose counter. The present invention also relates to a process for preparing such a pharmaceutical composition and its use in the treatment of respiratory disorders such as asthma in a subject in need thereof (e.g., a human).

BACKGROUND OF THE INVENTION

Various drug classes, such as corticosteroids, long acting β-agonists, and long acting muscarinic antagonists, are known for treatment of respiratory diseases. Fluticasone is an inhaled corticosteroid (ICS) used in treatment of respiratory diseases such as asthma and chronic obstructive pulmonary disease (COPD) in a subject (e.g., a human). A fluticasone metered dose inhaler is commercially marketed in United States by GlaxoSmithKline as FLOVENT® HFA which contains a microcrystalline suspension of fluticasone propionate in HFA-134a (1,1,1,2-tetrafluoroethane) and is supplied in a pressurized aluminum canister. Each canister is fitted with a dose counter and supplied with an actuator. FLOVENT® HFA is approved in three strengths: 44, 110 and 220 mcg per actuation.

In MDI formulations, where the drug is in suspended form, the particle size is controlled during manufacture by the size to which the solid medicament is reduced, usually by micronisation. However, if the suspended drug has the slightest solubility in the propellant, a process known as Ostwald ripening can lead to particle size growth. Also, particles may have a tendency to aggregate, or adhere to parts of the MDI, such as the canister or valve. The effect of Ostwald ripening, and particularly of drug deposition, may be particularly severe for potent drugs (including fluticasone propionate) which need to be formulated in low doses. Thus, it may be subject to considerable variability and is generally hard to control. The drug deposition occurring at the actuator orifice can lead to variability of doses and alter the performance of the device to aerosolize the formulation. Furthermore, the unintended deposition tends to reduce the amount of drug delivered to the lung and increase the amount ingested, potentially contributing to increased side effects.

Asthma patients unknowingly may run out of lifesaving medication because their metered dose inhalers do not include an integrated dose counter (see, e.g., Sander et al., *Annals of Allergy, Asthma & Immunology,* 2006; Volume 97; Page 34-38). Such incidences may be fatal during an asthma attack, because patients may misjudge the amount of drug left in their inhaler, and the inhaler may be empty at the time of the asthma attack. More recently developed metered dose inhalers are equipped with a lifesaving, vital component, i.e., a "dose indicator" or "dose counter". The "dose indicator" or "dose counter" records and displays the number of inhalation or "puffs" still remaining in the canister. Without a dose counter or dose indicator, there is no accurate or convenient way for patients to track the number of doses remaining in an inhaler. Addition of a "dose indicator" or "dose counter" to a metered dose inhaler presents several issues, such as placement in the actuator so as not to cause over/under counting and also to not impede the aerosol flow properties and is therefore challenging.

International Publication No. WO 01/19342 discloses a pharmaceutical formulation of fluticasone propionate, a propellant, a low volatility component and a solubilisation agent, where the fluticasone propionate is completely dissolved in the formulation.

International Publication No. WO 03/002169 discloses an aerosol actuator.

There is still, however, a need to develop a metered dose inhaler system comprising a pharmaceutical composition of fluticasone, or a pharmaceutically acceptable ester thereof, which is stable and overcomes the above mentioned issues and drawbacks of known systems.

SUMMARY OF THE INVENTION

The invention in one embodiment relates to a metered dose inhaler comprising (a) a stable pharmaceutical composition comprising fluticasone or its pharmaceutically acceptable ester (e.g., fluticasone propionate) and a propellant selected from hydrofluoroalkane (HFA) 227 and hydrofluoroalkane (HFA) 134a, (b) a canister, (c) a metering valve, (d) an actuator and (e) a dose counter.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter with a proviso that the dose counter is not attached directly or indirectly to canister.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the fluticasone or its pharmaceutically acceptable ester is present in suspended form in the composition.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the canister is a coated canister having part or all of its internal surfaces coated with a polymer blend comprising one or more fluorocarbon polymers. Alternatively, the inner surfaces of the canister may be anodized, plasma treated or plasma coated.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the metering valve has one or more sealing gaskets constructed substantially from ethylene propylene diene monomer (EPDM) rubber (e.g., the one or more sealing gaskets comprise greater than about 75%, greater than about 80%, greater than about 90% greater than about 95% or greater than about 99% EPDM rubber).

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (c) a dose counter, wherein the actuator has spray orifice diameter of about 550 μm to about 650 μm.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the actuator has a jet length of about 1.40 mm to about 1.60 mm.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the actuator has sump volume in the range of about 12 $mm^3$ to about 20 $mm^3$.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the actuator has sump volume in the range of about 15 $mm^3$ to about 17 $mm^3$.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the dose counter is located inside the actuator with the proviso that dose counter is not attached directly or indirectly to the canister.

Yet another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein fluticasone or its pharmaceutically acceptable ester (e.g., fluticasone propionate) has a $D_{90}$ particle size in the range of about 2 μm to about 4 μm.

In additional embodiments of any of the metered dose inhalers described herein, the metered dose inhaler exhibits dose content uniformity.

In additional embodiments of any of the metered dose inhalers described herein, each actuation delivers about 45 μL to about 65 μL volume of the pharmaceutical composition comprising fluticasone or its pharmaceutically acceptable ester (e.g., fluticasone propionate).

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister (c) a metering valve (d) an actuator and (e) a dose counter, wherein the metered dose inhaler delivers about 10 mcg to about 500 mcg, about 20 mcg to about 400 mcg, about 30 mcg to about 300 mcg, or about 40 mcg to about 250 mcg of fluticasone or its pharmaceutically acceptable ester (e.g., fluticasone propionate) per actuation.

In additional embodiments, any of the pharmaceutical compositions described herein may include from about 0.01% w/w to about 0.6% w/w, about 0.04% w/w to about 0.5% w/w, or 0.07% w/w to about 0.35% w/w of fluticasone or its pharmaceutically acceptable ester (e.g., fluticasone propionate), based on 100% total weight of the pharmaceutical composition.

Another embodiment relates to a metered dose inhaler comprising (a) a stable pharmaceutical composition comprising fluticasone or its pharmaceutically acceptable ester (e.g., fluticasone propionate) and a propellant selected from HFA 227, HFA 134a, and HFA 152a, (b) a canister, (c) a metering valve, (d) an actuator and (e) a dose counter wherein fluticasone or its pharmaceutically acceptable ester (e.g., fluticasone propionate) is present in suspended form in the composition.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the pharmaceutical composition is stable at 40°±2° C. and 75%±5% relative humidity (RH) for 6 months.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the pharmaceutical composition has a single maximum impurity in an amount of less than 0.1% and total impurity is not more than 1%, when stored for 6 months at accelerated conditions at 40°±2° C. and 75%±5% RH.

Another embodiment relates to a metered dose inhaler comprising (a) a stable pharmaceutical composition comprising fluticasone propionate and a propellant selected from HFA 227, HFA 134a and HFA 152a, (b) a canister, (c) a metering valve, (d) an actuator and (e) a dose counter, with the proviso that the dose counter is not attached directly or indirectly to canister, wherein the actuator has sump volume in the range of about 12 $mm^3$ to about 20 $mm^3$.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, wherein the pharmaceutical composition provides a mean median aerodynamic diameter (MMAD) of fluticasone or its pharmaceutically acceptable ester (e.g., fluticasone propionate) in the range of about 2 to about 4 μm.

Another embodiment relates to a metered dose inhaler comprising (a) a stable pharmaceutical composition comprising fluticasone propionate in an amount of about 30.8 μg to about 57.2 μg per actuation and a propellant selected from HFA 227 and HFA 134a, wherein the pharmaceutical composition provides a mean median aerodynamic diameter (MMAD) of fluticasone propionate in the range of about 2 to about 4 μm.

Another embodiment relates to a metered dose inhaler comprising (a) a stable pharmaceutical composition comprising fluticasone or its pharmaceutically acceptable ester or its pharmaceutically acceptable ester (e.g., fluticasone propionate) and a propellant selected from HFA 227 and HFA 134a, wherein the pharmaceutical composition provides a fine particle fraction (FPF) of fluticasone propionate in the range of about 30% to about 75%.

Another embodiment relates to a metered dose inhaler comprising (a) a stable pharmaceutical composition comprising fluticasone propionate in an amount of about 30.8 μg to about 57.2 μg per actuation and a propellant selected from HFA 227 and HFA 134a, wherein the pharmaceutical composition provides a fine particle fraction (FPF) of fluticasone propionate in the range of about 30% to about 75%.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, wherein the pharmaceutical composition provides a fine particle dose (FPD) of fluticasone propionate in the range of about 15 to about 30 μg.

Another embodiment relates to a metered dose inhaler comprising (a) a stable pharmaceutical composition comprising fluticasone propionate in an amount of about 30.8 μg to about 57.2 μg per actuation and a propellant selected from HFA 227 and HFA 134a, wherein the pharmaceutical composition provides a fine particle dose (FPD) of fluticasone propionate in the range of about 15 to about 30 μg.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, wherein the pharmaceutical composition provides a geometric standard deviation (GSD) of fluticasone propionate in the range of about 1 μm and about 2 μm.

Another embodiment relates to a metered dose inhaler comprising (a) a stable pharmaceutical composition comprising fluticasone propionate in an amount of about 30.8 μg to about 57.2 μg per actuation and a propellant selected from HFA 227 and HFA 134a, wherein the pharmaceutical composition provides a geometric standard deviation (GSD) of fluticasone propionate in the range of about 1 μm and about 2 μm.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, wherein the pharmaceutical composition has a single maximum impurity in an amount of less than 0.1% and total impurity is not more than 1%.

Yet another embodiment is a process for preparing a stable aerosol inhalation composition comprising fluticasone or a pharmaceutically acceptable ester thereof. In one embodiment the process comprises:

i) dispersing fluticasone or a pharmaceutically acceptable ester thereof (e.g., fluticasone propionate) in a first quantity of a propellant selected from HFA 227 and HFA 134a;
ii) homogenizing the mixture of step (i) to form a suspension;
iii) adding a second quantity of a propellant selected from HFA 227 and HFA 134a to the product of step (ii);
(iv) mixing and re-circulating the mixture of step (iii); and
(iii) filling the mixture of step (iv) into crimped canisters provided with a suitable valve. In one process embodiment, the propellant is HFA 134a.

Yet another embodiment, relates to a method of treating a respiratory disorder, such as asthma or COPD, in a subject (e.g., a human subject in need thereof) comprising administering the pharmaceutical composition as described herein.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the various embodiments of the invention.

DETAILED DESCRIPTION OF THE INVENTION

Figure 1:
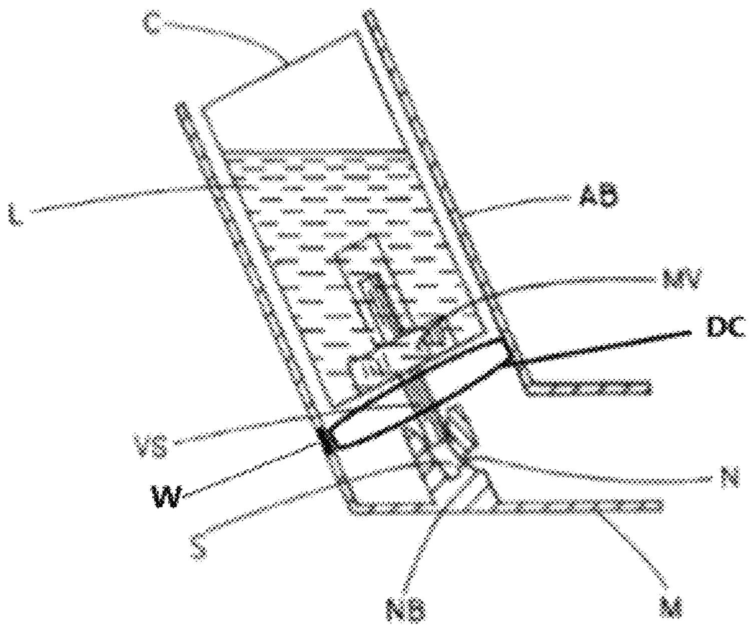
FIG. 1 shows a side view of a MDI, according to an embodiment of the present invention.

It is also to be understood that the terminology used herein is for describing particular embodiments only, and is not intended to be limiting. The term singular forms "a," "an" and "the" include plural references unless the context clearly dictates otherwise.

The term "stable pharmaceutical composition" as used herein means a pharmaceutical composition which exhibits any one or all of the following conditions: (i) the composition exhibits substantial chemical stability over a period of time such that it is suitable for aerosol inhalation administered by pressurized meter dose inhalers used for delivery of the drug to the respiratory tract, (ii) the composition is substantially resistant to one or more of aggregation, flocculation, and particle size changes and is capable of substantially maintaining the mass median acrodynamic diameter (MMAD) of suspending particles and the fine particle dose, (iii) the composition does not undergo phase separation by visual observation when stability is tested by shaking the composition (e.g., for 1 minute or shaken once or twice), and (iv) the composition does not exhibit phase separation when stored for at least 5 minutes, 10 minutes, 20 minutes, 30 minutes, 2 hours, 6 hours, 12 hours or 24 hours at ambient conditions (e.g., about 25° C. and a relative humidity (RH) of about 60%) or at accelerated conditions (e.g., at about 40° C. and about 75% RH). In some embodiments, a "stable" aerosol is one in which the fine particle fraction (FPF) or fine particle dose (FPD) of the aerosol does not change more than 15% or between 5-15% in 1 month from the initial FPF or FPD measured at ambient conditions (e.g., about 25° C. and a relative humidity (RH) of about 60%) or at accelerated conditions (e.g., at about 40° C. and about 75% RH). In another embodiment, a "stable pharmaceutical composition" is one in which the pharmaceutical composition has a single maximum impurity in an amount of less than 0.1% and a total impurity content of not more than 1%, for instance, when stored for 6 months at accelerated conditions at 40°±2° C. and 75%±5% RH.

The term "fluticasone" as used herein includes the base form and pharmaceutically acceptable salts, solvates, hydrates, enantiomers, esters, polymorphs, complex, and co-crystals thereof. Pharmaceutically acceptable esters of fluticasone include fluticasone propionate, fluticasone furoate and fluticasone valerate. In a preferred embodiment, fluticasone is present in any of the compositions described herein in the form of a propionate ester.

The term "active ingredient" (used interchangeably with "active" or "active agent" or "drug" or "medicament") as used herein include fluticasone or a pharmaceutically acceptable ester thereof (e.g., fluticasone propionate). The active ingredient may be present in respirable suspended form in the composition.

There are a number of routinely applied analytical tests for aerosol dosage forms for inhalation administration, including mass median aerodynamic diameter (MMAD), fine particle dose or fraction (FPD or FPF), and geometric standard deviation (GSD).

The term "mass median aerodynamic diameter (MMAD)" as used herein signifies the aerodynamic diameter at which half of the aerosolized drug mass lies below the stated diameter. Solid particles and/or droplets in an aerosol formulation can be characterized by their MMAD.

The term "fine particle fraction (FPF)" as used herein refers to mass fraction of the dose emitted in this size range by a particular inhaler. The fine particle fraction (FPF) is normally defined as the FPD divided by the emitted dose (ED) and expressed as a percentage. A higher fine particle fraction indicates improved delivery efficiency due to a significant decrease in throat deposition. Having a higher fine particle fraction may also allow a lower amount of total drug dose needed to achieve equivalent therapeutic benefits.

The term "fine particle dose" (also referred as FPD) is the total mass of active agent which is emitted from the device following actuation which is present in an aerodynamic particle size smaller than a defined limit.

The Geometric Standard Deviation (GSD) is a measure of the spread of an aerodynamic particle size distribution. Typically, GSD is calculated as follows:

$$GSD = (d_{84}/d_{16})^{1/2}$$

where $d_{84}$ and $d_{16}$ represent the diameters at which 84% and 16% of the aerosol mass are contained, respectively, in diameters less than these diameters.

As used herein, the term "average particle size" (or synonymously, "mean particle size") refers to the distribution of particles, wherein about 50 volume percent of all the particles measured have a size less than the defined average particle size value and about 50 volume percent of all measurable particles measured have a particle size greater than the defined average particle size value. This can be identified by the term "$D_{50}$" or "d (0.5)". Similarly, $D_{90}$ value relates to about 90 volume percent of all the particles measured have a size less than the defined particle size value (also referred to as "$D_{90}$ particle size"). The particle size can be measured using various techniques like laser diffraction, photon correlation spectroscopy (PCS) and Coulter's principle. In one embodiment, the aerosol particles of fluticasone or an ester thereof have an average particle size of 0.5 to 5 μm, such as 0.5 to 3 μm.

The term "respiratory disorder" as used herein includes pulmonary diseases involving any obstructive or destructive conditions of respiratory tract, vascular diseases and infectious diseases which may or may not be acute or chronic and communicable or non-communicable. The respiratory disorder may be chronic obstructive pulmonary disease (COPD), asthma, reactive airways dysfunction syndrome (RADS), acute respiratory distress syndrome (ARDS), irritant induced asthma, occupational asthma, sensory hyper-reactivity, airway (or pulmonary) inflammation, or multiple chemical sensitivity.

As used herein, the term "dose counter" is intended to refer to both dose counter devices and dose indicator devices.

Various analytical tests including, but not limited to, MMAD, FPD, FPF and GSD can be measured by various instruments such as Anderson Cascade Impactor. Anderson Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

A metered dose inhaler (MDI), according to one embodiment of the present invention, is shown in FIG. 1, and includes an Actuator, or Actuator Body AB in which is positioned a Canister C. Canister C contains a Liquid medicament L in suspension with a propellant. The most common propellants include fluorocarbons, HFA-134a or HFA-227. The canister possesses a Metering Valve MV for measuring discrete doses of the drug formulation fluid. A Valve Stem VS extends from the metering valve and acts as a conduit to pass the metered dose into a Nozzle Block NB situated in the actuator body, in which the valve stem is seated. The nozzle block has a passageway extending through it that forms an Expansion Chamber/Sump S in which the propellant formulation expands. A Nozzle channel N, which is aligned with a Mouthpiece opening M, exits the Expansion Chamber/Sump S, approximately tangential to the longitudinal axis of the axis of the valve stem. To use this type of MDI, the patient places the mouthpiece against their lips and actuates the MDI by depressing the canister into the actuator body AB. Upon actuation, a metered dose is measured by the metering valve MV and is expelled from the valve stem VS. The expelled dose passes into and through the Expansion Chamber/Sump S of the nozzle block NB and exits the nozzle block NB from the Nozzle channel N. A patient inhales through the mouthpiece opening M upon the release of the metered dose and inhales the drug dose as it exits the MDI.

Actuators used for the delivery of medicaments include a sump, located in a valve stem block adjacent to an actuator outlet. These sumps have angles and corners where the medicament being delivered can accumulate and/or deposit, giving rise to a reduction in the dose available and/or an increase in occurrence of blockage of a spray orifice. According to the present invention, the Sump S has an internal volume or sump volume smaller than 20 $mm^3$ and larger than 12 $mm^3$.

A Dose Counter DC is present inside the actuator body AB. In one embodiment, the dose counter DC is not attached directly or indirectly to the canister C. A Dose Counter Window W is located on an opposite side of the Mouthpiece opening M, or on a backside of the actuator.

Figure 2:
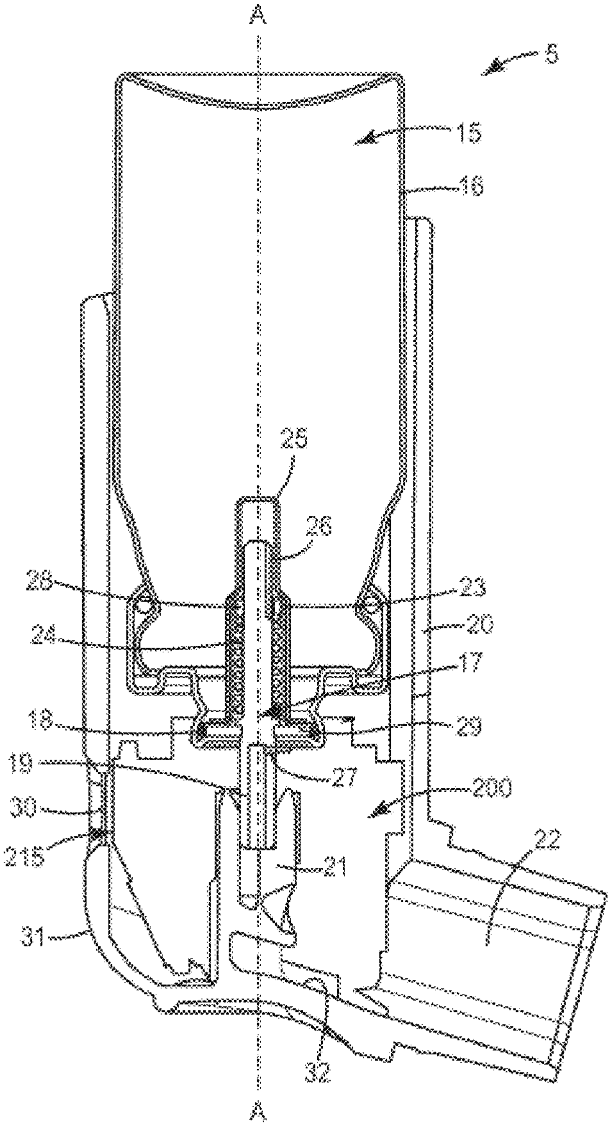
FIG. 2 shows a vertical cross section of a MDI, according to an embodiment of the present invention.

In one embodiment, according to the present invention, FIG. 2 shows a vertical cross-section through a Metered Dose Inhaler (5). The Metered Dose Inhaler (5) comprises the following components: a canister (15), an actuator (20) and a dose counter (200). The dose counter (200) is shown diagrammatically with its outer profile in an outline form. The canister (15) includes an aerosol container (16) equipped with a metering valve (17) secured via a ferrule (18). The metering valve (17) includes, inter alia, a valve stem (19), generally a valve body (23) defining a metering chamber, and a spring (24). The metering valve (17) may also include an outer valve body (25) serving as a bottle emptier and/or as defining a pre-metering chamber.

The container (16) contains an aerosol formulation of fluticasone propionate and a propellant selected from HFA 227 and HFA 134a. The actuator (20) and canister (15) are arranged so that the valve stem (19) engages with a nozzle block (21) provided within the actuator (20) so that the canister (15) is thus retained in the actuator (20).

In use (when the aerosol container (16) contains a medicament aerosol formulation), the user actuates the pressurized metered dose inhaler (5) to dispense a single dose of fluticasone propionate via the mouthpiece (22) by pressing down on the aerosol container (16) (referred to as an actuation stroke). Due to the fact that the valve stem (19) is held fixed by the nozzle block (21), and the aerosol container (16) moves downwardly when the user presses down on it (thus compressing the valve spring (24)), there is a relative reciprocal movement between the valve stem (19) and the aerosol container (16).

On this actuation (outward) stroke, once the aerosol container (16) moves sufficiently downwards, an inner groove (26) of the valve stem (19) is completely passed by an inner gasket seal (28), so that the metering chamber, defined by the valve body (23), is sealed off, and once the aerosol container (16) moves further sufficiently downwards, an opening (27) of an outer portion of the valve stem (19) is passed by an outer gasket (29), resulting in communication of the opening (27) with the metering chamber, defined by the valve body (23), so that the metering valve (17) will fire (dispense) a metered dose of fluticasone propionate (i.e. that quantity of formulation in the metering chamber).

After actuation, once the user releases the aerosol container (16), the aerosol container (16), on its return stroke, will move (under the force of the expansion of the spring (24)) upwardly, relative to the valve stem, back to its position of rest.

A bottom floor (32) of the actuator (20) provides a base for fitting of the dose counter (200). A longitudinal axis of reciprocal movement, between the metering valve, defined by the valve body (23), and the aerosol container (16) is labelled "A" (i.e. the first axis and also sometimes referred to as the actuation axis). As illustrated, the dose counter (200) is mounted within the interior of the actuator (20), generally positioned beneath the aerosol container (16), near and around the nozzle block (21). As shown in FIG. 2, the dose counter (200) may be provided with a window (215) to allow sight of indicia, where the indicia may be viewed through a window (30) in an actuator back wall (31). The dose counter (200), once mounted, desirably remains in position within the actuator (20), even when the aerosol canister (15) is removed, so that the dose counter (200) may not be removed by the user of the inhaler (5). The dose counter (200) is positioned around a nozzle block (21) of the actuator (20).

The Metered Dose Inhaler (5) comprises a suitable aerosol canister (16) with a metering valve (17) containing a stable pharmaceutical composition and an actuator (20) adapted to hold the aerosol canister (16) and allow for drug delivery. In another embodiment, an actuator with a spray orifice diameter of 400 μm to about 700 μm may be used in the invention. In one embodiment, the aerosol canister (16) in the drug delivery device has a head space representing greater than about 15% of the total volume of the canister (15).

In one embodiment, an actuator with a spray orifice aperture of about 550 μm to about 650 μm may be used in the invention. The choice of actuator plays an important role in drug delivery which in turn is dependent on various parameters like spray orifice aperture, jet length, stem block, sump geometry, sump volume and the like.

The stable aerosol inhalation composition or stable pharmaceutical composition of the present invention does not clog any part of the inhaler device, e.g., valve.

The canister may be made of any suitable material such as aluminium, aluminium alloys, stainless steel, tin, plastic or glass which may be coated or uncoated. Some drugs tend to adhere to the inner surfaces, i.e., walls of the canister, and may clog metering valves of the device components. This can lead to the patient getting significantly less than the prescribed amount of the active agent upon each activation of the MDI. Coating the inner surface of the container with a suitable polymer can reduce this adhesion problem. Suitable coatings include fluorocarbon copolymers such as FEP-PES (fluorinated ethylene propylene and polyethersulphone) and PFA-PES (perfluoroalkoxyalkane and polyethersulphone), epoxy and ethylene. Alternatively, the inner surfaces of the canister may be anodized, plasma treated or plasma coated. In an embodiment, the aerosol inhalation composition is filled into an aluminum canister whose inner surface is coated with a fluorocarbon polymer. The canister is fitted with a valve, preferably with a metering valve suitable to deliver a specific amount of the composition each time the device is actuated. Once a valve is crimped into place, the canisters must be able to adequately seal the propellant without leaking. In one embodiment, the metering valve delivers about 45 μl-65 μl of the composition. A gasket is also used between the metering valve and the canister to prevent leakage of the composition. In an embodiment, preferably, the gasket used is rubber or polymer gasket. In another embodiment, the gasket used is made of a material selected from POM (polyoxymethylene), COC (cyclic olefin copolymer), nitrile rubber, or any combination of any of the foregoing. In another embodiment, preferably, the gasket used is ethylene propylene diene monomer rubber.

The aerosol composition of the present invention may be placed in the canister using conventional methods such as cold filling or back filling or pressure filling leaving a sufficient "head space". The filled canisters are then placed in a suitable housing to complete the drug delivery device. In operation, when the canister is moved relative to the housing such that the metering valve is depressed, a fixed amount of composition is released initially through the metering valve and then though the cylindrical passage of the housing. As the propellant vaporizes, the drug is suspended in air. Patients then inhale the suspended drug, thereby effecting pulmonary drug administration.

In an embodiment, the stable aerosol inhalation composition as described herein is filled in a canister with the capacity of about 10 mL-22 mL wherein the filled volume of the composition is about 8 mL to about 20 mL. The actuator used for dispensing the drug delivers the volume of about 45 μl-65 μl per actuation. Patient may use one or two puffs once or twice daily as per the requirement or severity of disease.

A typical dose counter has a numerical display, indexes forward with each actuation, and has a discrete display that is often preferred by patients over a dose indicator. Dose indicators take many forms, but often count in multiples (for example, 10 or 20) or use colours to display remaining doses. They often do not index every count and require some patient interpretation of the display. The appeal of dose indicators tends to be the larger display and lower cost, although they are not considered by patients to be as accurate as a dose counter.

The dose counter or indicator may be located on a top, internal or side mounting of the MDI device. Top-mounted dose counters or indicators are attached to the MDI canister. An advantage of a top-mounted dose counter or indicator is that it can be added without affecting existing components, change of airflow through the actuator device, or pre-existing drug delivery. The two disadvantages are the overall height of the MDI, which is extended and has the potential to create difficulty for patients with a limited hand mobility or span; and the fact that the dose counter or indicator is exposed to the patient, which therefore means it must be designed to withstand a higher level of tampering and abuse.

Internal dose counters or indicators sit within the actuator and are often visible to the patient via a window in the actuator. Fitting a dose counter or indicator inside the actuator is a very difficult task, as the space envelope between the MDI valve and actuator is typically very small. An internal dose counter or indicator sits in the upstream airflow of the MDI, which has the potential to disrupt the spray plume. Another challenge is valve travel matching between the valve and dose counter or dose indicator.

According to one embodiment of the present invention, the internal Dose Counter is used in the metered dose inhaler and is located inside the actuator with the proviso that dose counter is not attached directly or indirectly to canister.

A propellant or HFA (hydrofluoroalkanc) propellant (also known as hydrofluorocarbon or HFC propellant) should be toxicologically safe and have a vapor pressure in order to enable the medicament to be administered via a pressurized MDI. Suitable HFA propellants include, but are not limited to, 1,1,1,2-tetrafluoroethane (HFA-134(a)), 1,1,1,2,3,3,3-heptafluoropropane (HFA-227), HFA-32 (difluoromethane), HFC-143(a) (1,1,1-trifluoroethane), HFC-134 (1,1,2,2-tetrafluoroethane), and HFA-152a (1,1-difluoroethane). In a preferred embodiment, the propellant is selected from 1,1,1,2-tetrafluorocthane (HFC-134(a)) and 1,1,1,2,3,3,3-heptafluoropropane (HFC-227). In a more preferred embodiment, the HFA propellant is HFA-134(a).

One embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter with a proviso that the dose counter is not attached directly or indirectly to canister.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter wherein fluticasone or its pharmaceutically acceptable ester is present in suspended form in the composition.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister (c) a metering valve (d) an actuator and (e) a dose counter, wherein the canister is a coated canister having part or all of its internal surfaces coated with a polymer blend comprising one or more fluorocarbon polymers. Alternatively, the inner surfaces of the canister may be anodized, plasma treated or plasma coated.

Another embodiment, relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the metering valve has one or more sealing gaskets constructed substantially from Ethylene Propylene Diene Monomer rubber.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the actuator has spray orifice diameter of about 550 μm to about 650 μm.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the actuator has sump volume in the range of 12 $mm^3$ to 20 $mm^3$.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein the dose counter is located inside the actuator with the proviso that dose counter is not attached directly or indirectly to canister.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister, (c) a metering valve, (d) an actuator and (e) a dose counter, wherein fluticasone propionate has $D_{90}$ particle size in the range of about 2 μm to about 4 μm.

In another embodiment, the metered dose inhaler exhibits dose content uniformity.

Another embodiment relates to a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister (c) a metering valve (d) an actuator and (e) a dose counter, wherein said metered dose inhaler delivers about 10 mcg to about 500 mcg or about 20 mcg to about 400 mcg or about 30 mcg to about 300 mcg or about 40 mcg to about 250 mcg of fluticasone or its pharmaceutically acceptable ester per actuation.

In another embodiment, the pharmaceutical composition may include from about 0.01% w/w to about 0.6% w/w or about 0.04% w/w to about 0.5% w/w or 0.07% w/w to about 0.35% w/w of fluticasone or its pharmaceutically acceptable ester, based on 100% total weight of pharmaceutical composition.

Another embodiment relates to an actuator which has one or more of following features:

a) spray orifice diameter of about 550 μm to about 650 μm;
b) sump volume in the range of about 12 $mm^3$ to about 20 $mm^3$; and
c) jet length of about 1.40 mm to about 1.60 mm.

Another embodiment relates to a metered dose inhaler comprising a) a stable pharmaceutical composition comprising fluticasone or its ester (e.g., fluticasone propionate) and a propellant selected from HFA 227 and HFA 134a, wherein fluticasone propionate has a $D_{90}$ particle size in the range of about 2 μm to about 4 μm; wherein fluticasone or its ester is present in suspended form in the composition;

b) a canister, wherein the canister is a coated canister having part or all of its internal surfaces coated with fluorocarbon polymer;

c) a metering valve, wherein the metering valve has one or more sealing gaskets constructed substantially from ethylene propylene diene monomer (EPDM);

d) an actuator, wherein the actuator has a spray orifice diameter of about 550 μm to about 650 μm, sump volume in the range of about 12 $mm^3$ to about 20 $mm^3$ and jet length of about 1.40 mm to about 1.60 mm; and e) a dose counter, wherein the dose counter is located inside the actuator with the proviso that dose counter is not attached directly or indirectly to canister.

In another embodiment, the aerosol composition of the present invention is prepared and filled in the appropriate canister. In one embodiment, the filling method comprises the following steps:

1. fluticasone or a pharmaceutically acceptable ester thereof (e.g., fluticasone propionate) is dispersed in a part quantity of propellant (preferably, HFA 134a) followed by homogenizing the mixture to form a suspension in manufacturing vessel.
2. The remaining quantity of propellant (preferably, HFA 134a) is added in the manufacturing vessel followed by mixing and re-circulation of the mixture.
3. The suspension obtained in step (2) is filled into crimped canisters provided with a suitable valve.

In an embodiment, a metered dose inhaler comprising (a) a stable pharmaceutical composition comprising fluticasone or its pharmaceutically acceptable ester (e.g., fluticasone propionate) and a propellant selected from HFA 227 and HFA 134a, (b) a canister (c) a metering valve (d) an actuator and (e) a dose counter, wherein the pharmaceutical composition is stable at 40°±2° C. and 75%±5% RH for 6 months.

Another embodiment relates to pharmaceutical composition which are found to be stable when stored at ambient (e.g., about 25° C. and a relative humidity (RH) of about 60%) or at accelerated conditions (e.g., at about 40° C. and about 75% RH) for at least 1 month. These compositions also exhibited good dose content uniformity (DCU), fine particle dose (FPD), and fine particle fraction (FPF). Preferably, such stable compositions provide acceptable dose content uniformity and/or do not show particle agglomeration after shaking (e.g., for 1 minute) for a period of at least 2 months, or at least 3 months or at least 6 months.

Another embodiment relates to a metered dose inhaler comprising (a) a stable pharmaceutical composition comprising (i) fluticasone or its ester and (ii) a propellant selected from hydrofluoroalkane (HFA) 227, and hydrofluoroalkane (HFA) 134a, (b) a canister, (c) a metering valve, (d) an actuator, and (e) a dose counter, wherein the dose counter is located inside the actuator and is not attached directly or indirectly to the canister.

The following examples are provided to enable one skilled in the art to practice the invention and are merely illustrative of the invention. The examples should not be read as limiting the scope of the invention.

EXAMPLES

Example (1-3) MDI Compositions Containing Fluticasone Propionate

Three MDI compositions were prepared as shown in Table 1.

TABLE 1

| | Composition (% w/w) | | |
|---|---|---|---|
| Ingredients | Example 1 44 mcg/ Actuation | Example 2 110 mcg/ Actuation | Example 3 220 mcg/ Actuation |
| Fluticasone Propionate | 0.08 | 0.17 | 0.33 |
| Propellant HFA 134a | 99.92 | 99.83 | 99.67 |

Manufacturing Process:

1. Fluticasone propionate was dispersed in a part quantity of HFA 134a followed by homogenizing the mixture to form a suspension in manufacturing vessel.
2. The remaining quantity of HFA 134a was added to the manufacturing vessel followed by mixing and re-circulation of the mixture.
3. The suspension obtained in step (2) was filled into crimped canisters provided with a suitable valve.

TABLE 2

Stability Data for Example 1 at 40° C. and 75% RH

| | Stability Data at 40° C. and 75% RH | | | |
|---|---|---|---|---|
| Test | Initial | 1 Month | 3 Month | 6 Month |
| FPD (μg) | 27.27 | 23.72 | 25.69 | 25.24 |
| FPF (%) | 62.91 | 55.60 | 59.12 | 59.39 |
| MMAD (μm) | 2.78 | 3.06 | 3.17 | 2.98 |
| GSD (μm) | 1.58 | 1.65 | 1.59 | 1.61 |
| Delivered Dose (μg) | 99.54 | 95.71 | 95.49 | 94.31 |
| Assay (%) | 99.90 | 105.10 | 89.44 | 102.53 |
| Single Max Impurity (%) | 0.04 | 0.03 | 0.06 | 0.04 |
| Total Impurity (%) | 0.07 | 0.08 | 0.35 | 0.31 |

TABLE 3

Stability Data for Example 1 at 25° C. and 60% RH

| | Stability Data at 25° C. and 60% RH | | | |
|---|---|---|---|---|
| Test | Initial | 3 Month | 6 Month | 12 Month |
| FPD(μg) | 27.27 | 27.68 | 22.47 | 24.34 |
| FPF (%) | 62.91 | 63.11 | 47.73 | 57.65 |
| MMAD (μm) | 2.78 | 2.95 | 3.33 | 2.98 |
| GSD (μm) | 1.58 | 1.57 | 1.65 | 1.63 |
| Delivered Dose (μg) | 99.54 | 94.27 | 93.57 | 97.69 |
| Assay (%) | 99.90 | 87.28 | 104.00 | 105.07 |
| Single Max Impurity (%) | 0.04 | 0.06 | 0.04 | 0.08 |
| Total Impurity (%) | 0.07 | 0.27 | 0.31 | 0.17 |

A bioequivalence study of Example 1 of Fluticasone Propionate MDI with FLOVENT® HFA 44 mcg was found satisfactory in 83 healthy subjects.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described above.

All publications, patents, and patent applications cited in this application are herein incorporated by reference to the same extent as if each individual publication, patent, or patent application was specifically and individually indicated to be incorporated herein by reference.

We claim:

1. A metered dose inhaler comprising:

a canister comprising an internal surface coated with a fluorocarbon polymer, the canister containing a pharmaceutical composition, the pharmaceutical composition comprising: fluticasone propionate that is in suspended form in the pharmaceutical composition; and a propellant, the propellant comprising at least one of hydrofluoroalkane 227 or hydrofluoroalkane 134a;

a metering valve in fluid communication with the canister, the metering valve being configured to meter a dose of the pharmaceutical composition out of the canister, the metering valve comprises: a valve stem defining a conduit; and at least one sealing gasket, the at least one sealing gasket being made of at least one of ethylene propylene diene monomer, cyclic olefin copolymer, or a combination thereof;

an actuator configured to receive the dose of the pharmaceutical composition from the metering valve and to deliver the dose of the pharmaceutical composition to a user, the actuator comprises a valve stem block, a jet, and a spray orifice, the valve stem block defining a sump; and a dose counter connected to the metering valve, the dose counter being configured to indicate a number of doses remaining in the canister, wherein:

the dose counter is inside the actuator, the spray orifice has a diameter between about 550 μm and about 650 μm, inclusive, the jet has a length between about 1.40 mm and about 1.60 mm, inclusive, and the sump has a volume between 15 $mm^3$ and 17 $mm^3$, inclusive.

2. The metered dose inhaler of claim 1, wherein the fluorocarbon polymer is at least one of (i) fluorinated ethylene propylene and polyethersulphone or (ii) perfluoroalkoxyalkane and polyethersulphone.

3. The metered dose inhaler of claim 1, wherein the canister is made of a metal.

4. The metered dose inhaler of claim 1, wherein the pharmaceutical composition comprises the fluticasone propionate in an amount of from about 0.01% w/w to about 0.6% w/w based on a total weight of the pharmaceutical composition.

5. The metered dose inhaler of claim 4, wherein the pharmaceutical composition comprises the fluticasone propionate in an amount of from about 0.07% w/w to about 0.35% w/w based on a total weight of the pharmaceutical composition.

6. The metered dose inhaler of claim 1, wherein the pharmaceutical composition has a single maximum impurity in an amount of less than 0.1% and total impurity in an amount less than 1%, when stored for 6 months at accelerated conditions at a temperature of 40°±2° C. and a relative humidity of 75%±5%.

7. The metered dose inhaler of claim 1, wherein the dose counter is positioned beneath the canister.

8. The metered dose inhaler of claim 1, wherein the dose counter is positioned around a nozzle block of the actuator.

9. The metered dose inhaler of claim 1, wherein the dose counter comprises indicia and a window that allows sight of the indicia.

10. The metered dose inhaler of claim 1, wherein the pharmaceutical composition is prepared by a process comprising:

dispersing fluticasone propionate in a part of hydrofluoroalkane 134a to form a suspension;

adding remaining part of hydrofluoroalkane 134a to the suspension and re-circulating the suspension to form a final suspension; and filling the suspension into canisters provided with a valve.

* * * * *